(12) United States Patent
Wu

(10) Patent No.: US 7,059,854 B2
(45) Date of Patent: Jun. 13, 2006

(54) ABUTMENT STRUCTURE USED EXCLUSIVELY IN TOOTH IMPLANTATION

(76) Inventor: Wen-Yuen Wu, 11Fl., No. 320, Dashuen 1st Rd., Tzuoying Chiu, Kaohsiung (TW), 813

(*) Notice: Subject to any disclaimer, the term of this patent is extended or adjusted under 35 U.S.C. 154(b) by 171 days.

(21) Appl. No.: 10/325,729

(22) Filed: Dec. 23, 2002

(65) Prior Publication Data
US 2004/0121285 A1 Jun. 24, 2004

(51) Int. Cl.
*A61C 8/00* (2006.01)

(52) U.S. Cl. .................................. 433/173; 433/172
(58) Field of Classification Search ............... 433/172, 433/173, 174, 175, 176
See application file for complete search history.

(56) References Cited

U.S. PATENT DOCUMENTS

| 4,177,562 A | | 12/1979 | Miller et al. ................. 433/174 |
| 4,799,886 A | * | 1/1989 | Wimmer ....................... 433/176 |
| 5,030,095 A | | 7/1991 | Niznick ........................ 433/173 |
| 5,071,345 A | | 12/1991 | Rosen ........................... 433/17 |
| 5,110,292 A | * | 5/1992 | Balfour et al. ............... 433/173 |
| 5,524,749 A | | 6/1996 | Thompson et al. ........... 206/38 |
| 5,620,323 A | * | 4/1997 | Bressman et al. ........... 433/174 |
| 5,725,378 A | | 3/1998 | Wang ........................... 433/173 |

* cited by examiner

*Primary Examiner*—John J Wilson
(74) *Attorney, Agent, or Firm*—Bacon & Thomas (57) ABSTRACT

A dental abutment is provided with an axial through hole and is fastened at a lower segment thereof with an implant in conjunction with a cement which is infected into a threaded hole of the implant. An excess amount of the cement is forced out via the axial through hole of the abutment such that the cement is deposited on a flat top of the abutment to facilitate the removing of the cement residue and to minimize the likelihood of a gums inflammation which may be resulted from an incomplete removal of the cement residue.

7 Claims, 11 Drawing Sheets

ABUTMENT STRUCTURE USED EXCLUSIVELY IN TOOTH IMPLANTATION

FIELD OF THE PRESENT INVENTION

The present invention relates generally to a tooth implantation, and more particularly to an abutment structure which is designed to enhance efficiency of the tooth implantation, and to minimize the likelihood of the postoperational gums inflammation which is resulted from an incomplete removal of cement.

BACKGROUND OF THE PRESENT INVENTION

Figure 1:
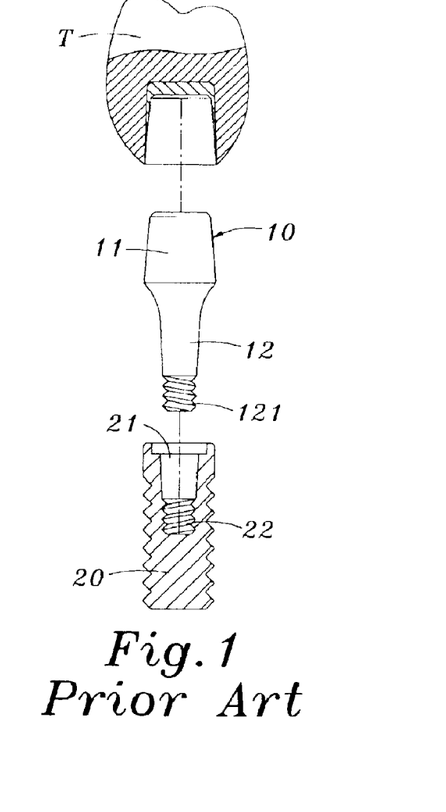
FIG. 1 is a schematic view of a conventional abutment, along with an implant.

Referring to FIG. 1 of the drawing, a prior art dental abutment 10 has an upper segment 11, and a lower segment 12 which is provided at the free end with male threads 121. The upper segment 11 is dimensioned to fit into a tooth "T", while the lower segment 12 is fastened with an implant 20 such that the male threads 121 of the lower segment 12 are engaged with female threads 22 of a cavity 21 of the implant 20. The engagement is reinforced by a cement "G" which is injected into the cavity 21.

Figure 2:
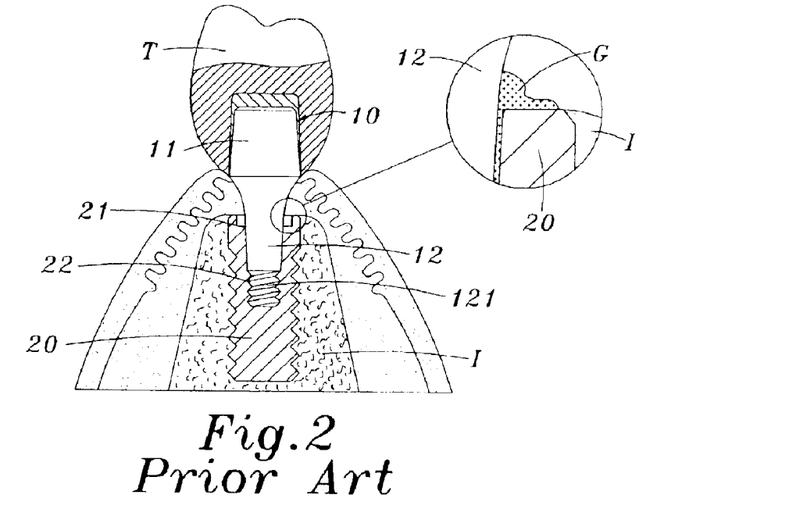
FIG. 2 is a sectional schematic view of the conventional abutment which is implanted into a socketed bone in conjunction with the implant.

As shown in FIG. 2, a socketed bone "I" is provided with a socket into which the implant 20 is fitted. In other words, the tooth "T" is implanted in the bone "I" in conjunction with the abutment 10 and the implant 20. In view of the fact that the application of the cement "G" can not be easily controlled with precision in terms of quantity of the cement "G", it is therefore likely that an excessive amount of the cement is injected into the cavity 21 of the implant 20, thereby resulting in the spilling of the cement "G". The cement residue is often deposited on the outer surface of the lower segment 12 of the abutment 10, as well as on the top end of the implant 20, as shown in an enlarged view of a circled portion of FIG. 2. In the event that the cement residue is not removed properly, the socketed bone "I" and the tissue surrounding the socketed bone "I" will fail to grow together intimately. Such a mishap often results in a gums inflammation, or a situation in which the implant 20 is apt to become loosened by a chewing action. In order to avert such an operational deficiency as described above, a complete removal of the cement residue from the lower segment 12 of the abutment 10 and the top end of the implant 20 is called for at the expense of the patient.

Figure 3A:
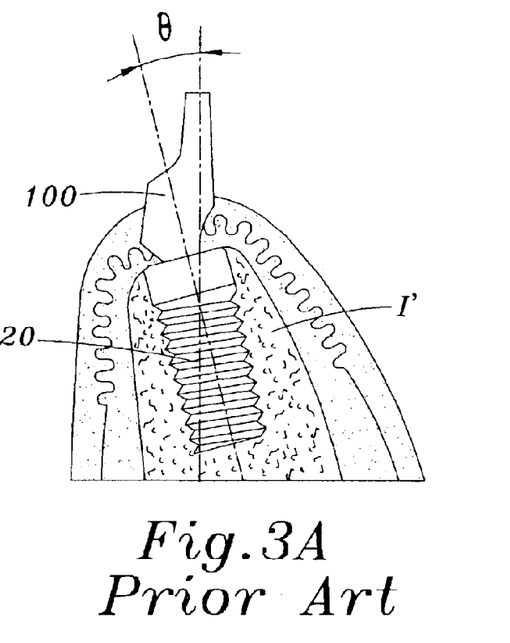
FIG. 3A is a schematic view of the conventional abutment which is implanted into an incisor socketed bone in conjunction with the implant at implantation angle θ.
Figure 3B:
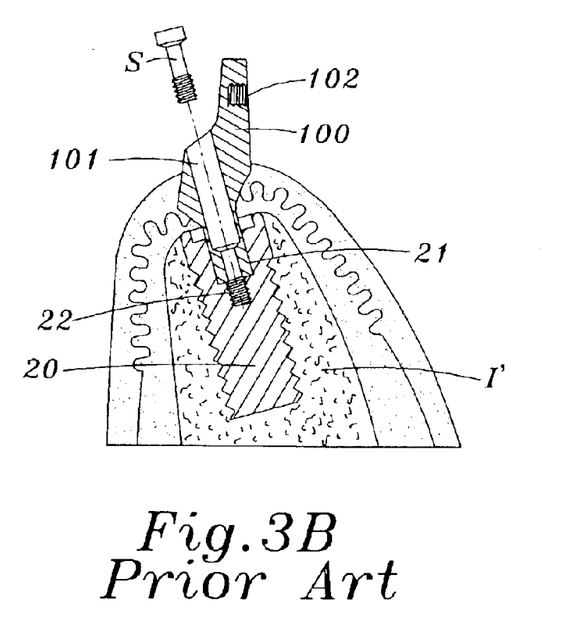
FIG. 3B is a schematic view of the conventional abutment which is implanted into an incisor socketed bone in conjunction with the implant, according to the above prior art abutment of FIG. 3A.
Figure 3C:
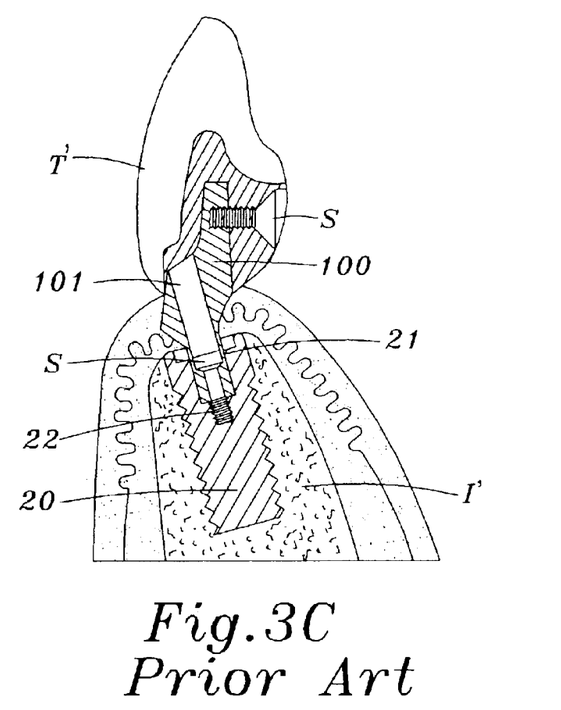
FIG. 3C is a schematic view of the conventional abutment which is implanted into an incisor socketed bone in conjunction with the implant, according to the above prior art abutment of FIG. 3B.

The abutment 10 described above is used in an upright manner in the molar implantation; nevertheless it is not suitable for use in the incisor implantation. As shown in FIGS. 3A, 3B, and 3C, the socketed bone "I" of the incisor has an inclination. Accordingly, the implant 20 must be inserted into the socketed bone "I" at an angle θ corresponding to the inclination of the socketed bone "I", as shown in FIG. 3A. As a result, an abutment 100 with an inclination is used to implant an incisor "T". The abutment 100 is provided in the center with an axial through hole 101 and is fastened with the implant 20 by a fastening screw "S" which is engaged with the female threads 22 of the cavity 21 of the implant 20 via the axial through hole 101 of the abutment 100, as illustrated in FIG. 3B. The abutment 100 is further provided in the lateral side of the upper segment thereof with a lateral threaded hole 102. The abutment 100 is fastened with the incisor "T" by another fastening screw "S" which is engaged with the lateral threaded hole 102, as shown in FIG. 3C.

Figure 4A:
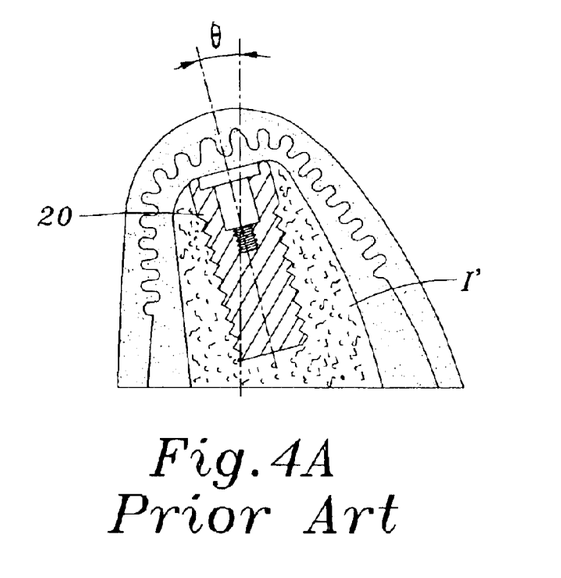
FIG. 4A is a sectional schematic view of the conventional implant which is inserted into the incisor socketed bone with the implantation angle θ.
Figure 4B:
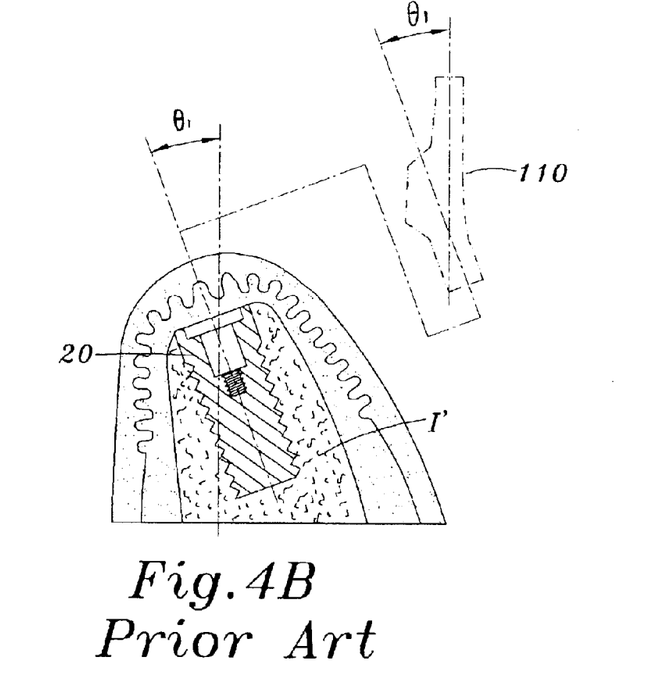
FIG. 4B is a sectional schematic view of the conventional implant which is inserted into the incisor socketed bone with the implantation angle θ1.
Figure 4C:
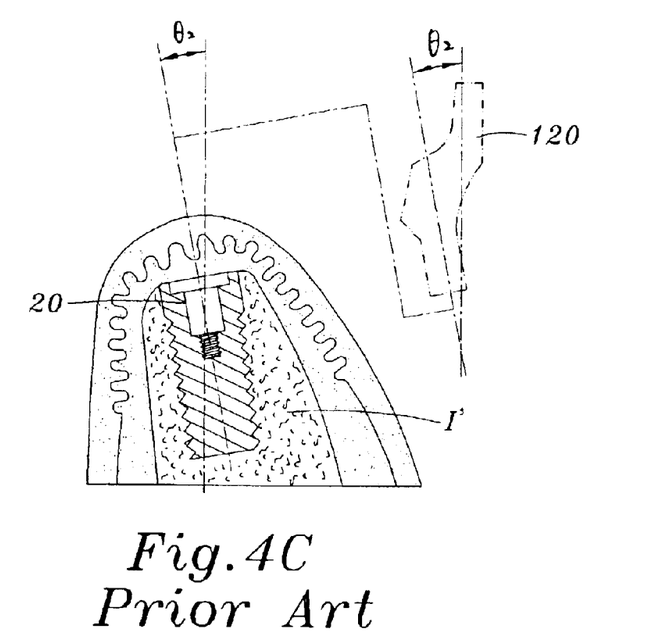
FIG. 4C is a sectional schematic view of the conventional implant which is inserted into the incisor socketed bone with the implantation angle θ2.

Referring to FIG. 4A of the drawing, the implantation angle θ is likely deviated in the implantation operation of the implant 20 such that the implantation angle θ1 may be too large, as shown in FIG. 4B, or that the implantation angle θ2 may be too small, as shown in FIG. 4C. Such angular deviations as described above often result in failure of implantation. With the purpose of overcoming the drawback of the angular deviation, a variety of abutments 100, 110, 120, etc, must be prepared at additional cost, which is of course passed on to the patient under treatment. The pre-operational X-cay diagnosis is of a little help in determining the implantation angle of the implant 20 in conformity with the specification of the abutment 100. In addition, there is lack of a standardized implantation method by which the implant 20 is always implanted into the socketed bone "I" at a correct angle. As a result, the abutment 100 must be mended by the dental technician at additional cost.

SUMMARY OF THE PRESENT INVENTION

The main objective of the present invention is to provide an abutment, which is provided in the center with an axial through hole enabling the excess amount of cement to be discharged from the upper segment of the abutment, thereby averting the deposit of the cement residue in the outer surface of the lower segment of the abutment and in the top of an implant. The cement residue can be thus easily removed to prevent the gums inflammation.

Another objective of the present invention is to provide an abutment structure comprising a crown and a fixation pin. The crown and the upper segment of the abutment are fastened together by the fixation pin and can be removed for cleaning.

Another objective of the present invention is to provide an abutment structure comprising a crown and a fixation pin, by which the abutments of various inclinations can be used in the implantation of an implant into an incisor socketed bone without the angular deviation. The abutment can be joined together with the crown by the fixation pin in various manners, thereby reducing the cost of molding the artificial tooth as well as the abutment inventory.

The features, functions and advantages of the present invention will be more readily understood upon a thoughtful deliberation of the following detailed description of the preferred embodiments of the present invention with reference to the accompanying drawings.

DETAILED DESCRIPTION OF THE PREFERRED EMBODIMENT

Figure 5:
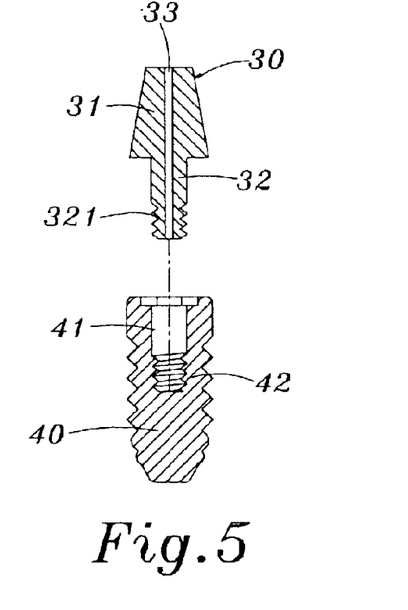
FIG. 5 is a schematic plan view of an abutment structure, along with an implant, according to a first preferred embodiment of the present invention.

Referring to FIG. 5 of the drawing an abutment structure according to a first preferred embodiment of the present invention is illustrated. The abutment 30 has an upper segment 31 which is of conical construction and is provided with a flat top. The abutment 30 has a lower segment 32 which is or a columnar construction and is smaller in diameter than the upper segment 31. The lower segment 32 is provided at a bottom end with male threads 321. The lower segment 32 is further provided in the center with an axial through hole 33 extending through the bottom end of the lower segment 32 toward the top of the upper segment 31. As illustrated, the axial through hole has a uniform diameter along its length.

Figure 6:
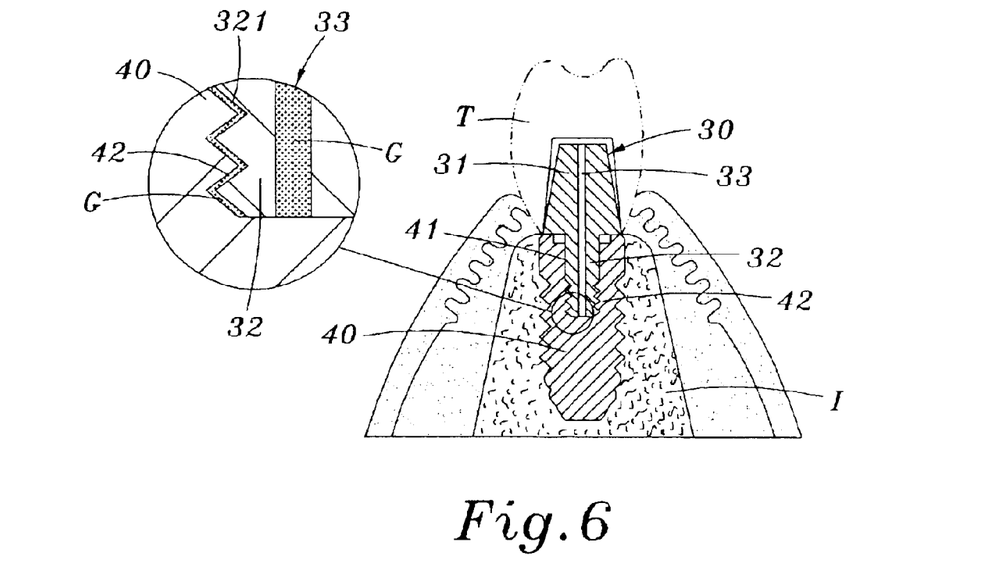
FIG. 6 is a sectional schematic of an abutment structure, which is joined with the implant, according to the above first preferred embodiment of the present invention.

As shown in FIG. 6, the implantation according to a preferring embodiment of the present invention is similar in operation to the current tooth implantation. An implant 40 is first inserted into a socketed bone I. The implant 40 is provided With a threaded hole 41 into which a cement G is injected. The abutment 30 is then joined with the implant 40 such that the male threads 321 of the lower segment 32 of the abutment 30 are engaged with the female threads 42 of the threaded hole 41 of the implant 40, and that the tip of the lower segment 32 comes in contact with the bottom end of the threaded hole 41. The engagement of the male threads 321 with the female threads 42 is reinforced by the cement G. The excess amount of the cement G is forced out of the threaded hole 41 via the axial through hole 33 of the abutment 30, as shown in an enlarged view of FIG. 6. The excess amount of the cement is thus discharged and then deposited on the top of the upper segment 31 of the abutment 30. As a result, the cement deposit can be easily removed without impairing the surrounding gums tissue.

Figure 7A:
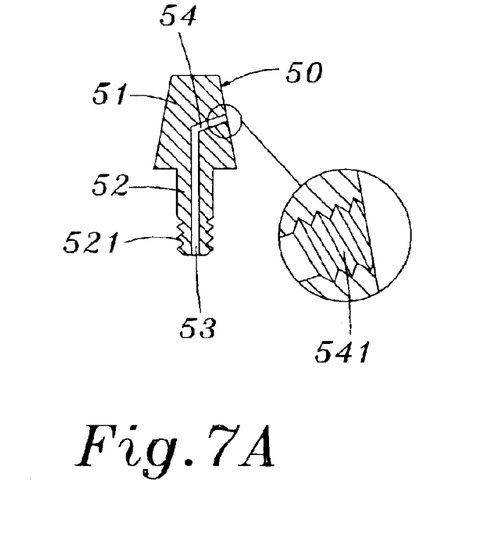
FIG. 7A is a sectional schematic view of an abutment structure, according to a second preferred embodiment of the present invention.
Figure 7B:
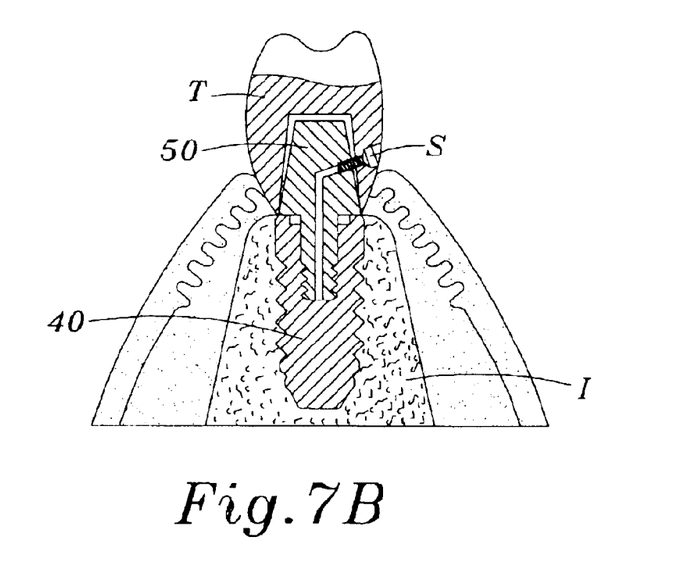
FIG. 7B is a sectional schematic of an abutment structure, which is joined with the implant, according to the above second preferred embodiment of the present invention.

Referring to FIGS. 7A and 7B of the drawings, an abutment 50 according to a second preferred embodiment of the present invention is illustrated. The abutment 50 has a lower segment 52 which is provided in the center of the bottom end thereof with an axial hole 53. The abutment 50 has an upper segment 51 which is provided with a radial hole 54 in communication with the axial hole 53. The radial hole 54 is provided with female threads 541 and fastened the tooth T with the upper segment 51 of the abutment 50 by a screw S.

Figure 8A:
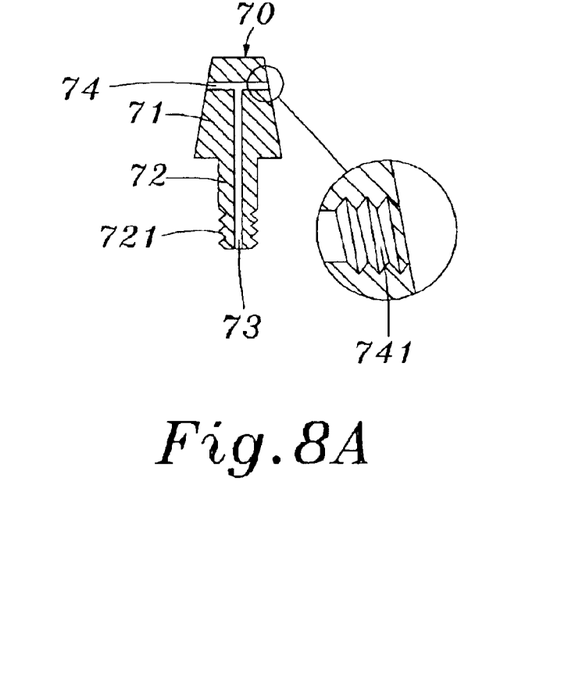
FIG. 8A is a sectional schematic view of an abutment structure, according to a third preferred embodiment of the present invention.
Figure 8B:
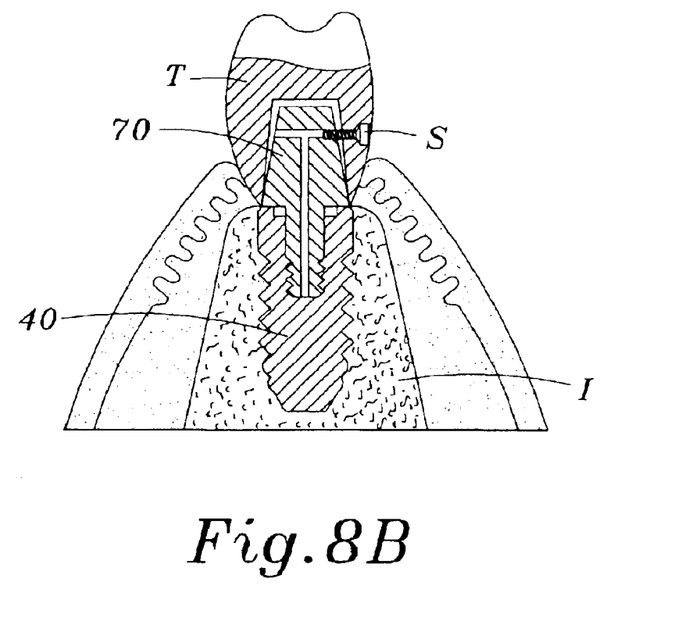
FIG. 8B is a sectional schematic of an abutment structure, which is joined with the implant, according to the above third preferred embodiment of the present invention.

As shown in FIGS. 8A and 8B, an abutment 70 according to a third preferred embodiment of the present invention is illustrated. The abutment 70 has a lower segment 72 which is provided in the center of the bottom end thereof with an axial hole 73.

The abutment 70 further has an upper segment 71 which is provided with a radial through hole 74 in communication with the axial hole 73. The radial through hole 74 is provided in one end with female threads 741 and fastened the tooth T with the upper segment 71 of the abutment 70 by a screw S.

Figure 9:
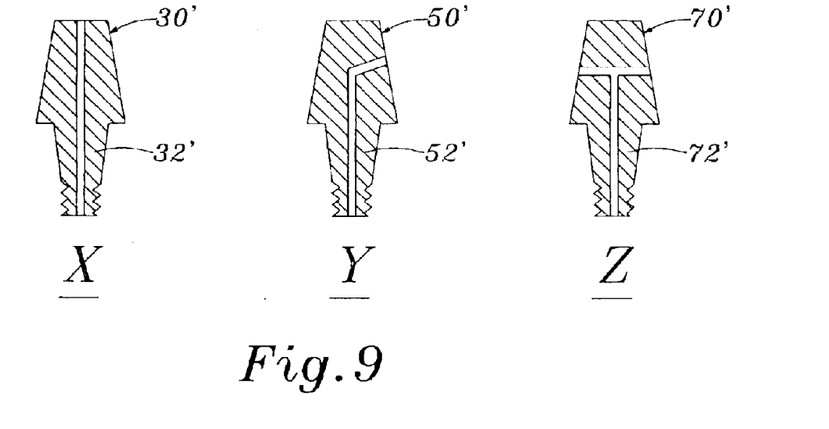
FIG. 9 is a sectional schematic view of the lower segment of an abutment structure, according to the above each preferred embodiment of the present invention.

As shown in FIG. 9, the abutments 30', 50', and 70' according to the above each preferred embodiment of the present invention is illustrated, the abutments 30', 50', and 70' have respectively an inverted conical lower segment 32', 52', 72'.

Figure 10:
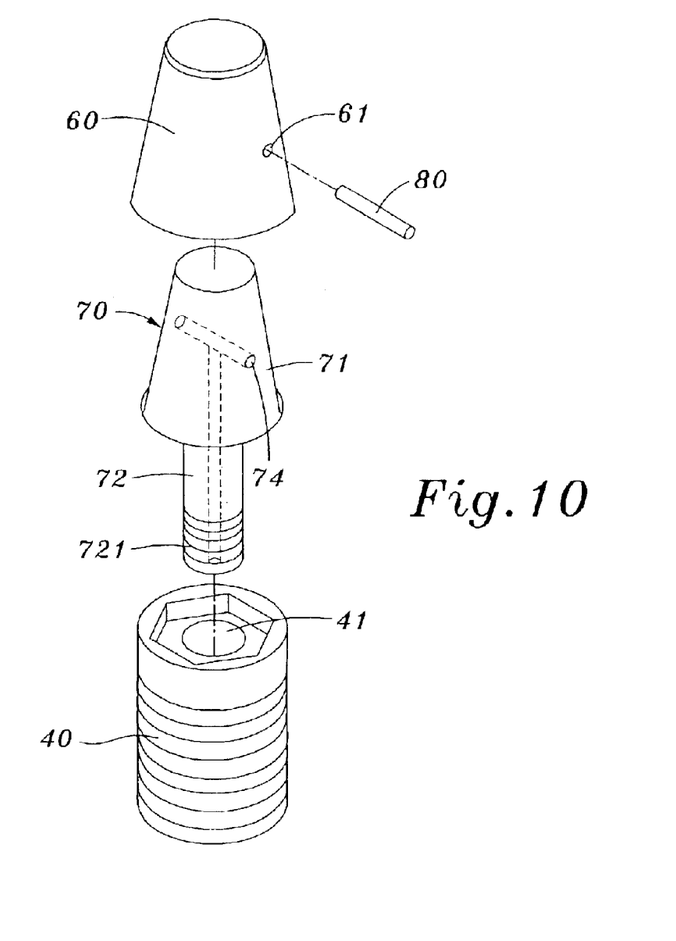
FIG. 10 is an exploded view of an abutment structure, along with a crown and a fastening pin, according to a fourth preferred embodiment of the present invention.

As shown in FIG. 10, an abutment structure according to a fourth preferred embodiment of the present invention is illustrated. The abutment structure comprises an abutment 70, a crown 60, and a retention pin 80. The crown 60 is a hollow conical construction and is provided with a flat top. The crown 60 is fitted over an upper segment 71 of the abutment 70. The upper segment 71 is provided with a radial through hole 74. The crown 60 is provided with two radial through holes 61 corresponding to the radial through hole 74 of the upper segment 71. The crown 60 is fastened with the upper segment 71 of the abutment 70 by the retention pin 80 which is put through the radial through holes 61 and 74.

Figure 11A:
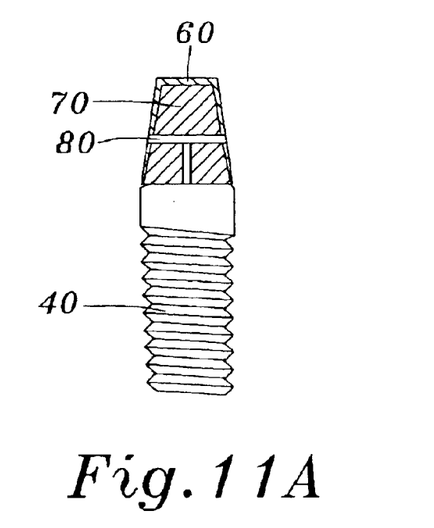
FIG. 11A is a sectional schematic view of an abutment structure, which is joined with the implant and the crown, according to the above fourth preferred embodiment of the present invention.
Figure 11B:
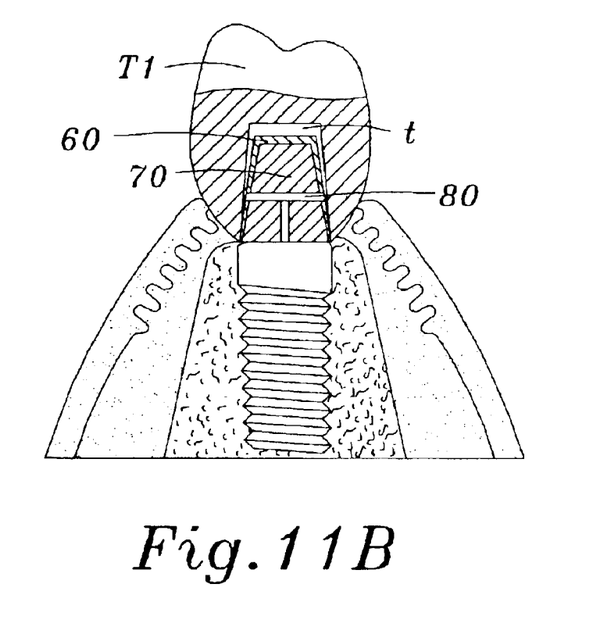
FIG. 11B is a sectional schematic view of an abutment structure, which is used in a molar tooth implantation, according to the above fourth preferred embodiment of the present invention.

Referring to FIGS. 11A, and 11B of the drawings, the abutment 70 according to the fourth preferred embodiment of the present invention is illustrated. The abutment 70 is used in a molar tooth implantation in which the crown 60 is first fitted over the upper segment 71 of the abutment 70 such that the crown 60 is so turned as to enable the two radial through holes 61 of the crown 60 to be in alignment with the radial through hole 74 of the upper segment 71 of the abutment 70, The crown 60 is then fastened with the upper segment 71 by the retention pin 80 which is received in the radial through holes 61 and 74.

The crown 60 serves as an inner crown t of the abutment 70 to facilitate the molding of a tooth T1, as shown in FIG.

Figure 12A:
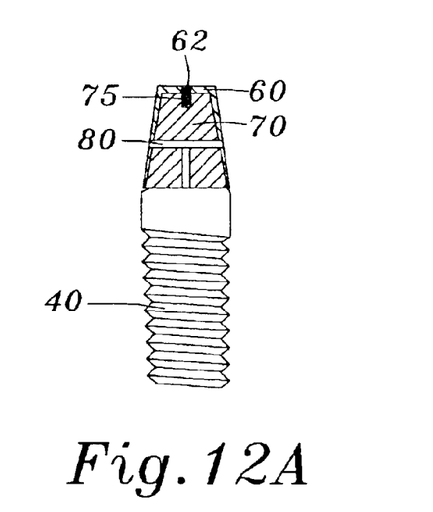
FIG. 12A is a sectional schematic view of an abutment structure, which is joined with the crown by a screw, according to the above fourth preferred embodiment of the present invention.
Figure 12B:
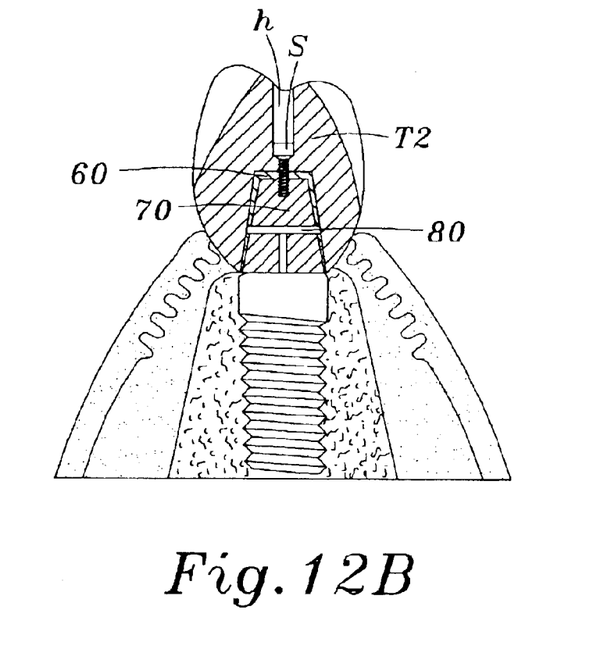
FIG. 12B is a sectional schematic view of an abutment structure, which is used in a molar tooth implantation, according to the above fourth preferred embodiment of the present invention of FIG. 12A.

11B. The tooth T1 is detachable. In the event that the tooth T2 is fixed, the crown 60 and the abutment 70 is respectively provided with a threaded hole 62 and 75 for fastening tooth T2 with the crown 60 by a fastening screw S which is engaged with the threaded hole 62 and 75, as shown in FIGS. 12A and 12B.

Figure 13:
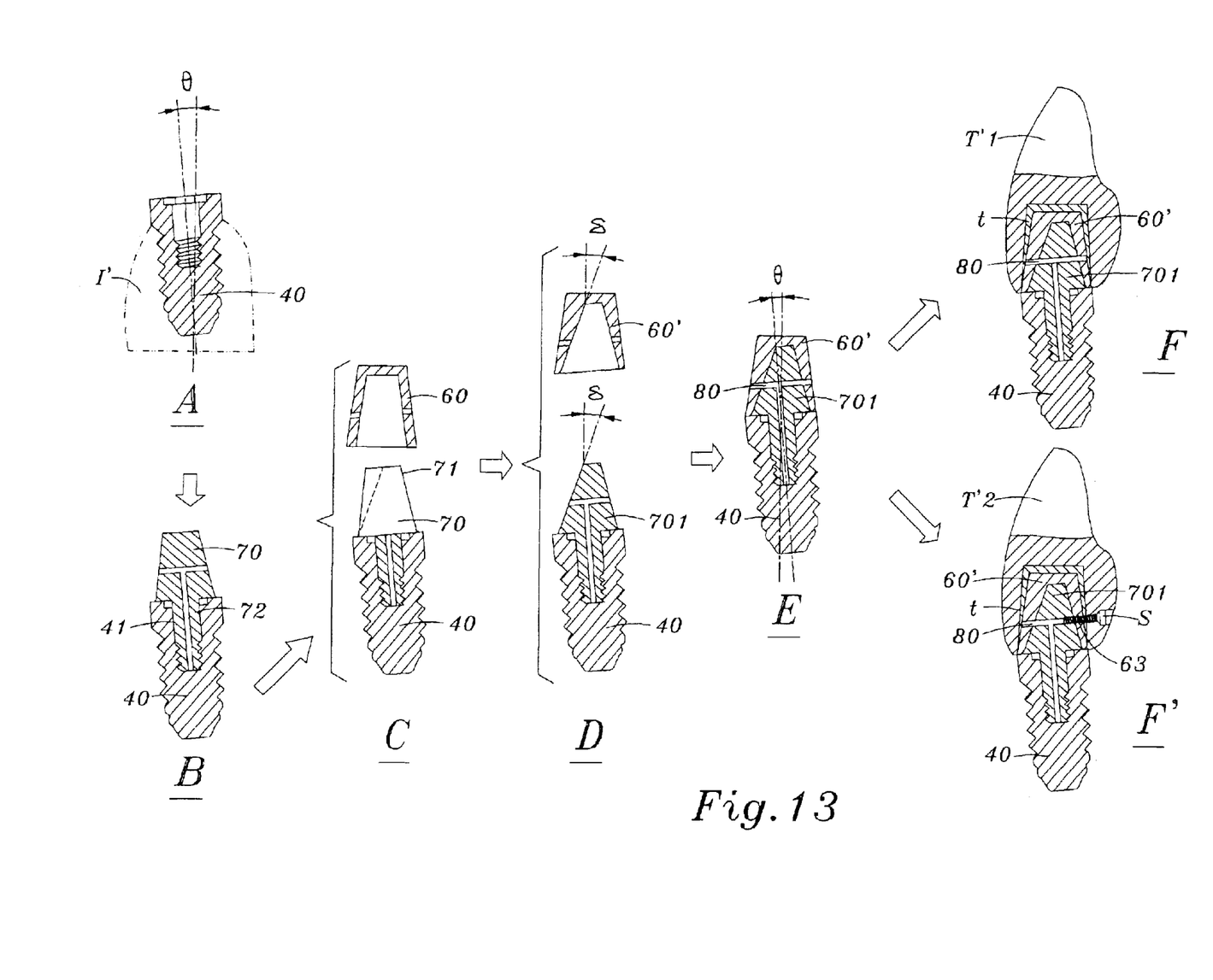
FIG. 13 is a series of schematic views regarding the steps by which the present invention is embodied.

As shown in FIG. 13, the crown 60 and the abutment 70 of the present invention is used in the implantation of an incisor tooth, the following steps are taken.

a. The dentist in charge of the implanting operation does not have to calculate precisely the implanting angle θ. The dentist should be able to insert an implant 40 into an incisor socketed bone I', as shown in A view of FIG. 13.

b. Upon completion of the fusion of the implant 40 with the tissue of the incisor socketed bone I', the lower segment 72 of the abutment 70 is fastened into an inner cavity 41 of the implant 40, as shown in B view of FIG. 13.

c. The dentist determines and marks an inclination area on the upper segment 71 of the abutment 70, as indicated by the doted lines in C view of FIG. 13. before the abutment 70 is so turned as to separate from the implant 40. The abutment 70 with the marked inclination area, the crown 60, and the retention pin 80 are then processed and finished by the dental technician such that an abutment 701 with a desired inclination δ, and a crown 60' with a desired inclination δ are produced, as shown in D view of FIG. 13.

d. The abutment 701 and the crown 60' are fastened together by the retention pin 80 such that the crown 60' is kept in an upright position, as shown in E view of FIG. 13.

e. If an incisor tooth T'1 is to be detachable, the crown 60' serves as an inner crown of the abutment 701. They are processed by the dental technician to form an outer crown t of the incisor tooth T'1, as shown in F view of FIG. 13.

f. If an incisor tooth T'2 is to be fixed, the crown 60' is provided by drilling with a threaded hole 63, and the fastening of the crown 60' with the incisor tooth T'2 is done with a fastening screw S, as illustrated in F' view of FIG. 13.

The embodiments of the present invention described above are to be regarded in all respects as being illustrative and nonrestrictive. Accordingly, the present invention may be embodied in other specific forms without deviating from the spirit thereof. The present invention is therefore to be limited only by the scopes of the following claims.

What is claimed is:

1. An abutment structure comprising:
    an upper segment of a conical construction and having a flat top, said upper segment provided in a periphery with a radial hole; and
    a lower segment of a columnar construction and smaller in diameter than said upper segment, said lower segment being provided at a bottom end with male threads and an axial hole having a uniform diameter extending through the bottom end of said lower segment and toward said flat top of said upper segment such that said axial hole is in communication with the radial hole of said upper segment.

2. An abutment structure, as recited in claim 1, wherein the radial hole of said upper segment is provided with female threads which is contiguous to the outer end of the radial hole.

3. An abutment structure, as recited in claim 1, further comprising a crown and a retention pin, wherein said crown being of a hollow conical construction and provided with a flat top, said crown being fitted over the upper segment of said abutment and further provided in a periphery with a through holes corresponding to the radial hole of said upper segment.

4. An abutment structure comprising:
    an upper segment of a conical construction and having a flat top, said upper segment provided with a radial hole; and
    a lower segment of a columnar construction and smaller in diameter than said upper segment, said lower segment being provided at a bottom end with male threads and an axial hole having a uniform diameter extending through the bottom end of said lower segment and toward said flat top of said upper segment such that said axial hole is in communication with said radial through hole of said upper segment.

5. An abutment structure, as recited in claim 4, wherein said radial through hole of the upper segment is provided in one end with female threads.

6. An abutment structure, as recited in claim 4, wherein said lower segment of said abutment is of an inverted conical construction.

7. An abutment structure, as recited in claim 4, further comprising a crown and a retention pin, wherein said crown being of a hollow conical construction and provided with a flat top, said crown being fitted over the upper segment of said abutment and further provided in a periphery with a through holes corresponding to said two radial through holes of the upper segment.

* * * * *